United States Patent [19]

Terpstra et al.

[11] Patent Number: 6,093,450
[45] Date of Patent: *Jul. 25, 2000

[54] METHOD FOR MANUFACTURING A FIBER-REINFORCED BIOACTIVE CERAMIC IMPLANT

[75] Inventors: Rinse Alle Terpstra, Geldrop; Yvette Gertrude Roman, Meteren; Klaas Timmer, Bilthoven; Harmen Anne Meinema, Leusden, all of Netherlands

[73] Assignee: Nederlandse Organisatie voor toegepast-natuurwetenschappelijk onderzoek TNO, Netherlands

[*] Notice: This patent issued on a continued prosecution application filed under 37 CFR 1.53(d), and is subject to the twenty year patent term provisions of 35 U.S.C. 154(a)(2).

[21] Appl. No.: 08/994,880

[22] Filed: Dec. 19, 1997

[30] Foreign Application Priority Data

Dec. 30, 1996 [NL] Netherlands ............... 1004867

[51] Int. Cl.⁷ ............... A61L 13/00; B05D 3/00; C23C 16/00
[52] U.S. Cl. .................. 427/255.24; 427/2.26; 427/2.27; 427/255.38; 427/255.395
[58] Field of Search ............. 427/255, 255.2, 427/255.6, 255.3, 2.26, 2.27, 255.24, 255.28, 255.38, 255.395

[56] References Cited

U.S. PATENT DOCUMENTS

| | | | |
|---|---|---|---|
| 4,459,708 | 7/1984 | Buttazzoni | 3/1.91 |
| 4,636,218 | 1/1987 | Fukuura et al. | 623/18 |
| 4,917,702 | 4/1990 | Scheicher et al. | 623/16 |
| 4,994,414 | 2/1991 | Yamamoto et al. | 501/12 |
| 5,000,746 | 3/1991 | Meiss | 604/304 |
| 5,062,798 | 11/1991 | Tsuge et al. | 433/201.1 |
| 5,080,589 | 1/1992 | Oden et al. | 433/202.1 |
| 5,108,436 | 4/1992 | Chu et al. | 623/66 |
| 5,164,363 | 11/1992 | Eguchi et al. | 427/255.2 |
| 5,167,271 | 12/1992 | Lange et al. | 164/103 |
| 5,204,314 | 4/1993 | Kirlin et al. | 427/255.2 |
| 5,205,716 | 4/1993 | Georges et al. | 416/229 A |
| 5,258,029 | 11/1993 | Chu et al. | 623/16 |
| 5,451,434 | 9/1995 | Doellein | 427/255.2 |
| 5,639,402 | 6/1997 | Barlow et al. | 264/6 |
| 5,642,996 | 7/1997 | Mochida et al. | 433/174 |
| 5,744,075 | 4/1998 | Klett et al. | 264/29.6 |
| 5,766,669 | 6/1998 | Pugh et al. | 427/2.27 |

FOREIGN PATENT DOCUMENTS

| | | |
|---|---|---|
| 0405634 | 1/1991 | European Pat. Off. . |
| 0411208 | 2/1991 | European Pat. Off. . |
| 900874 | 8/1990 | WIPO . |

OTHER PUBLICATIONS

G.C. Allen, et al,; "Surface and Bulk Study of Calcium Phosphate Bioceramics Obtained by Metal Organic Chemical Vapor Deposition", Nuclear Instruments & Methods in Physics Research, Section B: Beam Interactions with Materials and Atoms, vol. 116 1996, pp. 457–460 1996 (No month).

Chemical Abstracts, vol. 126, No. 6 Feb. 10, 1997, abstracts no. 78837.

Masaki, Akitatsu et al.: Ceramic–base Composite Materials Having BN Interfaces and Their Preparation.

*Primary Examiner*—Diana Dudash
*Attorney, Agent, or Firm*—Londa & Gluck LLP

[57] ABSTRACT

The invention relates to a method for manufacturing a fiber-reinforced bioactive ceramic implant, wherein a base form is made from fibrous material and interspaces between the different fibers are filled using chemical vapor phase infiltration. Preferably, a calcium-phosphate compound is brought between the fibers, which are preferably of the continuous-fiber type.

8 Claims, No Drawings

METHOD FOR MANUFACTURING A FIBER-REINFORCED BIOACTIVE CERAMIC IMPLANT

BACKGROUND OF THE INVENTION

This invention relates to a method for manufacturing a fiber-reinforced bioactive ceramic composite material, and to the use of this material as implant.

In the prior art different materials have already been proposed for making implants therefrom for incorporation into animal bodies, and in particular into the human body. Such materials are required to meet various, highly stringent standards.

In the first place, these materials must be biocompatible, in order that rejection phenomena in the body do no occur or do so to the least possible extent.

Further, certain mechanical properties are required, specific mention being made of a high toughness of fracture and a low modulus of elasticity comparable to that of human bone tissue.

Many of the bone implants used heretofore are made of metal. Apart from the mechanical properties of metal, which do not correspond to a desirable extent with those of animal bone tissue, such implants must be replaced after 10 to 15 years owing to corrosion, which is an evident disadvantage.

The current generation of polymeric materials which have been developed for implantation purposes possess a desired toughness. However, the biocompatibility of these materials leaves to be desired, so that rejection phenomena cannot be precluded.

Ceramic materials, by contrast, are eminently biocompatible. This holds in particular for calcium-phosphate-ceramics. However, ceramic materials have as a disadvantage that they have a brittle fracturing behavior.

It has been proposed in the prior art to improve the toughness of fracture of ceramic material by incorporating fibers. It is in this field that the present invention resides.

The known methods for manufacturing fiber-reinforced ceramic material for implantation purposes have a number of evident disadvantages associated with the filling of the spaces between the fibers with ceramic material. This filling of the spaces between the fibers with ceramic material will be designated in this description by the term "densification".

According to the first methods for manufacturing fiber-reinforced ceramic material, a fiber construction was contacted with powdered precursor material for forming ceramics. Then this whole was subjected to a sintering step, with ceramic being formed from the precursor material. This sintering step, however, has as an important disadvantage that it entails much shrinkage and hence deformation of the product contemplated. This occurrence of shrinkage makes the near-net-shape formation of the implants considerably more difficult. Indeed, it is of great importance for the bio-implant to have exactly the right dimensions, especially so because the finished ceramic product does not readily allow of any mechanical processing operation.

A general description of this type of conventional techniques for manufacturing ceramic matrix composites is given in K. K. Chawla, "Ceramic matrix composites", Chapman & Hall, London (1993), Chapter 4: *"Processing of ceramic matrix composites"*. Further, reference is made to T. N. Tiegs, P. F. Becker, "Sintered $Al_2O_3$—SiC-whisker composites", Am.Ceram.Soc.Bull. 66 [2] (1987) 339–342. In this article $Al_2O_3$ powder is mixed with SiC whiskers (monocrystal fibers of a diameter of about 0.6 μm and a length of 10–80 μm) and other additions. A liquid medium is added, followed by drying, pressing and sintering under an argon atmosphere (1 atm.) at 1700–1800° C. The shrinkage and deformation problem to which reference is made, is discussed, for instance, in the standard ceramic processing reference J. S. Reed, "Introduction to the principles of ceramic processing", John Wiley & Sons, New York (1988), Chapter 26: *Firing processes*.

A densification technique which has been developed to solve the problem of shrinkage is the so-called "hot pressing". In this technique the sintering step is carried out under such pressure that volume contraction hardly occurs, if at all. However, hot pressing is applicable to a limited extent only, because only simply shapes can be manufactured. Again, reference is made to Chapter 26 of the Reed textbook.

In addition, it is known that fibrous structures can be densified by the sol/gel technique. In such a technique the fibrous material is contacted with a colloidal solution of the starting materials for the ceramic densification material. By evaporation this solution is converted to a homogeneous gel. The gel is then converted to a solid material by heating at high temperatures in the presence of oxygen.

These steps must be repeated a number of times because the respective transitions from sol to gel to solid successively entail volume reductions. In practice, it has been found that it is not possible with this technique to fully close the spaces between the fibers. This gives rise to weak spots in the fiber-reinforced ceramic material, which can cause fracture upon loading. (A. Nazeri, E. Bescher, J. D. Mackenzie, "Ceramic composites by the sol-gel method: a review", Ceram.Eng.Sci.Proc. 14 [11–12] (1993) 1–19)

In addition, techniques are known for applying a ceramic layer to a shaped substrate. For instance, in the article by Spoto et al. in J. Mater. Chem. 4 (1994) 1849–1850 and in the article by Allen et al. in Nuclear Instruments & Methods in Physics Research, Section B: Beam Interactions with materials and Atoms, p. 116 (1996) pages 457–460, methods are described for coating a substrate with hydroxyapatite by Chemical Vapor Deposition (CVD). Thus a coating is formed which consists of a different material than the substrate to which it has been applied. In such products which possess a layered structure, the bond between the different materials remains a critical point. All this limits the use of these products for implantation purposes.

In fact, in the body many implants are exposed to a high degree of loading, with a large number of different forces acting on the implant. Owing to differences in the mechanical properties of the materials applied onto each other, the bond is thereby weakened. The bond may even be broken, with all adverse consequences for a patient.

SUMMARY OF THE INVENTION

The object of the present invention is to provide a homogeneous fiber-reinforced bioactive ceramic product that can be used for implantation purposes, and which does not present the problems of the prior art. The term 'bioactive implant' in this description and the appended claims is understood to mean an implant provoking a specific, biological reaction at the interface between the tissue of an organism and the implant material, which reaction results in the formation of a bond between the tissue and the implant material. Physical characteristics of bioactive implant include a mechanically strong bond with surrounding, living tissue and provide a means of helping a body in a recovery process.

This object is achieved by densifying a fiber structure using chemical vapor phase infiltration.

DETAILED DESCRIPTION OF THE INVENTION

Accordingly, the invention relates to a method for manufacturing a fiber-reinforced bioactive ceramic material, wherein a base form is made from a fibrous material and interspaces between the different fibers are filled using chemical vapor phase infiltration.

Using the method according to the invention the densification of a fiber preform is carried out with chemical vapor phase infiltration (CVI). Since this technique does not entail any sintering step, the problem of shrinkage does not arise.

In this technique the ceramic material is brought between the fibers on a molecular level. Strength problems arising through the introduction of liquid or gel-like media, in particular the unintended and uncontrolled creation of (macro)pores, can therefore be prevented.

It is noted that the chemical vapor phase deposition process is known per se. This technique has been developed from the CVD process. While in the CVD process a layer is applied to the substrate, in CVI a substrate is uniformly impregnated. Fibers are coated with material deposited from a vapor until the spaces between the fibers are filled up.

Such a technique has been described by Y. G. Roman and R. A. Terpstra in a review article in Ceramic Technology International 1996, 113–116, Ed. Ian Birkby; Sterling Publications Ltd. London.

This article describes ceramics reinforced with continuous fibers and presently used in the aerospace industry.

In CVI a porous substrate, for instance a fiber structure, is infiltrated with a gas phase in a reactor. In this gas phase the components are present which are needed for the ceramic product to be formed. Then the elements in the gas phase are excited in such a manner that they react to form a solid product on the fiber surface.

An important condition for carrying out CVI is finding suitable reaction conditions under which a uniform deposition can be achieved at acceptably high reaction rates in the complete volume between the fibers of a preform.

It is preferred to use a starting substance which contains all matrix elements. In the case of an SiC-matrix the starting material is, for instance, $SiCH_3Cl_3$.

For forming a biocompatible bioactive ceramic material, in particular calcium-phosphate compounds, suitable single-source precursors are not available. Specifically, calcium- and phosphorus-containing compounds are not volatile enough, not stable enough and/or unsuitable in composition to deposit a desired compound.

Little is known about depositing metal phosphates by chemical vapor phase reactions, using a single-source precursor. As far as is known, only the deposition of chromium, molybdenum and tungsten phosphates from the complex of the formula $M(CO)_5(PH)_3$, wherein M represents Cr, Mo or W, has been described (I. M. Watson et al. Thin Solid Films 201 (1991), 337). Corresponding complexes of calcium are not known.

According to the present invention, presently suitable gas mixtures and suitable reaction conditions have been found which enable the manufacture of fiber-reinforced bioactive ceramics, with the spaces between the fibers being densified with calcium-phosphate compounds.

The ceramic material that is used according to the invention to densify the spaces between the fibers are salts of the general formula

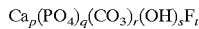

wherein $p \geq 1$ and q, r, s and $t \geq 0$, and
wherein $2p=3q+2r+s+t$. When p=10, q=6, r=0, s=2 and t=0, the above-mentioned formula gives the structural formula of hydroxyapatite, which is preferably used. If p=1, q=0, r=1 and s=0 calcium carbonate is represented; and when, for instance, p=9, q=5, r=1 and s=1 and t=0 a carbonate-containing hydroxyapatite is obtained. (E. J. Donahue, D. M. Schleich, Mat.Res.Bull. 26 (1991) 1119–1126, describe vapor phase processes whereby CaO and $CaCO_3$ are deposited from $Ca(dpm)_2$ (=$Ca(tmhd)_2$).

From the prior art CVD processes are known whereby specifically calcium-containing superconductive materials, such as $Tl_2Ba_2CaCu_2O_x$ and $Bi_2Sr_2CaCu_2O_x$, are deposited from the vapor phase. The calcium precursors used here, viz. fluorine-free and fluorine-containing Ca-β-diketonates, are also usable in the method according to the invention.

In this light reference can be made to L. M. Tone, D. W. Richeson, T. J. Marks, J. Zhao, J. Zhang, B. C. Wessels, H. O. Marcy, C. R. Kannewurf, "Organometallic chemical vapor deposition Strategies and progress in the preparation of thin films of superconductors having high critical temperatures", Adv. Chem. Series 226 (1990), 351–368. Here a calcium-β-diketonate, $Ca(dpm)_2$, is used as calcium precursor for the deposition of the systems Tl—Ba—Ca—Cu—O and Bi—Sr—Ca—Cu—O. The separate known fluorine-free and fluorine-containing Ca-β-diketonate precursors can be used separately in the method according to the present invention.

In a preferred embodiment the starting material is a gas mixture in which either $Ca(tmhd)_2$ (calcium bis-2,2,6,6-tetramethyl-3,5-heptanedionate; identical to $Ca(dpm)_2$, calcium dipivaloylmethane), or $Ca(hfac)_2$ (calcium bis-1,1,5,5,5-hexafluoro-2,4-pentanedionate), preferably $Ca(hfac)_2\cdot triglyme$ or $Ca(hfac)_2\cdot tetraglyme$, is used as calcium precursor.

$Ca(tmhd)_2$ contains only calcium, carbon, oxygen and hydrogen atoms. This compound is preferably used for the formation of hydroxyapatite. From this product CaO is deposited. $Ca(tmhd)_2$ is commercially available, for instance from Aldrich. However, the inventors have found that the quality of this commercially available product is not sufficient for depositing a pure product. A prior purification by sublimation, whereby the sublimate is maintained under a dry nitrogenous atmosphere is therefore desired. For that matter, it is also possible to synthesize $Ca(tmhd)_2$ under dry conditions from pure $CaH_2$ and Htmhd.

$Ca(hfac)_2$, in triglyme or tetraglyme form, also contains fluorine atoms and deposits $CaF_2$. It is useful for depositing fluorapatite. These products can be synthesized by a one-on-one reaction of $Ca(hfac)_2$ with triglyme and tetraglyme, respectively, for instance according to European patent application 90201485.1.

Other suitable precursors of calcium are fluorine-free and fluorine-containing Ca-β-diketonate compounds and triglyme and tetraglyme complexes thereof such as $Ca[RC(O)CHC(O)R']_2$, $Ca[RC(O)CHC(O)R']_2.triglyme$ and $Ca[RC(O)CHC(O)R']_2.tetraglyme$, wherein, for instance, (fluorine-free) $R=R'=CH_3$; $R=R'=t$—Bu; $R=CH_3$, $R'=tBu$; and, for instance (fluorine-containing) $R=R'=CF_3$; $R=CH_3$, $R'=CF_3$; $R=n-C_3F_7$, $R'=tBu$. See: European patent applications 90201485.1 and 92307490.0.

As already indicated hereinabove, not much is known about the vapor deposition of metal phosphates. In the above-mentioned article by Spoto et al. in J. Mater. Chem. $P_2O_5$ is used as source of phosphorus. This compound has an evaporation temperature of 270° C.

Phosphorus precursors that have a lower evaporation temperature are alkyl phosphites of the general structure P(OR)$_3$ or alkyl phosphates of the general structure OP(OR)$_3$, wherein R represents a low, C$_{1-6}$ saturated or unsaturated and/or branched alkyl group, and preferably methyl or ethyl. In addition, the chlorine-containing compounds PCl$_3$ and POCl$_3$ can be used as phosphorus precursor, although these compounds are rather hydrolysis-sensitive.

By starting from pure starting material, very pure bioceramics can be made.

In the method according to the invention first a base form of fibrous material is made. This base form determines the eventual shape of the implant to be manufactured. The spaces between the fibers are filled up.

In fact, any fibrous material that is compatible with the ceramics to be infiltrated and that is stable during the reaction conditions during the CVI step can be used. Specifically, ceramic fibers, glass fibers, carbon fibers and organic polymeric fibers are suitable, preferably fibers of carbon, hydroxyapatite, aluminum oxide, zirconium oxide, glass or metal fibers, such as inter alia Fecralloy®.

The method according to the invention makes it possible to employ long or continuous fibers as fibrous material. This provides great advantages as regards the mechanical properties, in particular toughness, of the implant to be manufactured.

At the relatively high sintering temperature such as it is employed in the known sintering technique, by contrast, the continuous fibers lose a large part of their mechanical properties owing to growth of granules and creep. If during such a densification in addition high pressures (hot pressing) are employed, the fibers will further be subjected to mechanical loading as well and consequently fracture and sustain damage. Obviously, this is not beneficial to the properties of the composite.

Through a suitable choice of the type and the orientation of the fibrous material, the stiffness (modulus) of the implant can be optimized in any desired direction.

The base form, which must possess a certain dimensional stability, can be manufactured in a conventional manner, for instance using textile techniques. See, for instance, F. K. Ko, "Preform fibre architecture for ceramic matrix composites", Ceramic Bulletin 68 [2] (1989) 4021–413.

In the reactor, in which a base form from fibrous material is present, gaseous precursors for the ceramics are introduced. By choosing the pressure of the gas streams and the reactor temperature to be favorable, the gases diffuse through the base form of fibrous material. In the base form the gases react to form a solid. It is of great importance here that the conditions are selected such that the matrix deposits homogeneously in the entire volume of the fibrous substrate with acceptable rates.

The method according to the invention, wherein a base form from fibrous material is densified with a ceramic material, has as an advantage that it is carried out under mild conditions, such as a relatively low densification temperature. As a result, the fibrous structure is not, at least less readily, damaged. The infiltration or densification temperature in the CVI reactor is between 200 and 1200° C., preferably between 300 and 900° C., most preferably between 350 and 800° C. The infiltration or densification temperature can be set at a value during the reaction, that is, can follow a gradient. The pressure in the CVI reactor is preferably between 1 mbar-5 bar (absolute), preferably between 1 mbar and 1 bar (absolute). The precursor mole fraction is preferably between 0.05 and 1, preferably between 0.5 and 1, while the total gas flow regime is preferably between 1 ml/min to 10,000 ml/min (STP) and more preferably between 100 and 1000 ml/min (STP).

It is noted that international patent application 90/08745 discloses a method in which a form part based on pyrocarbon is manufactured. This form part, which can be used in cardiac valves, is manufactured by coking carbon fibers at 800–1200° C. and subsequently infiltrating this product with pyrocarbon at about 1100° C., whereafter the product is sealed with a layer of pyrocarbon at a temperature of between 1300 and 1800° C. Such carbon-carbon composites cannot actively participate in processes in the body and are therefore not bioactive. Further, during the high infiltration temperatures the fibers lose a great part of their mechanical properties, so that the composite end product is not comparable in terms of properties with the products that are obtained according to the invention.

The method of the invention makes it possible to control the porosity of the infiltrated material without the mechanical properties being adversely affected. In particular, this occurs by slowly growing a ceramic coating on the fibers. According as the infiltration lasts longer, the coating grows on longer, until the complete porosity is filled up. By ending the infiltration process prematurely, the composite still retains a certain porosity. Moreover, by selecting the proper process conditions, the manner in which the growth proceeds in terms of pore size distribution can be controlled as well. Some degree of porosity provides that a better bonding between the implant and tissue is accomplished. In particular, some degree of porosity provides the possibility of systemic tissue growing in.

According to a preferred embodiment, the fibrous material is densified in two steps, the first step consisting in carrying out a sol/gel technique, and the second step consisting in carrying out CVI. This embodiment provides a method which allows the densification to be carried out faster. First a coarse infiltration with a sol/gel technique, for instance that described in the publication of Takahashi et al. in Eur. J. Solid State Inorg. Chem. 32 (1995) 829–835, is carried out, whereafter the coarse structure is further densified using CVI.

The present invention will now be elucidated in and by the following, non-limiting examples.

EXAMPLE 1

Use is made of the apparatus described in Chapter 3 of the above-mentioned thesis by Roman. Two-dimensional wovens of carbon fibers (Toray Industries Inc.; Torayra T-300) are wetted with acetone to prevent breakage of the fibers. Thereafter these wovens are cut to size and stacked onto each other, with the successive layers having a different orientation relative to each other (turned through 45° relative to the preceding layer), in order to obtain as much isotropy as possible. These stacked layers constitute the preform. The preform is placed in a graphite holder.

In the underside of this preform holder, holes have been drilled to lead gaseous/vaporous reactants into the preform. The top of the preform holder, which is open in known applications, is closed off with a (graphite) cover in which holes have been drilled to lead unreacted reactants and gaseous/vaporous reaction products out of the preform. The cover can be screwed fixedly to the preform holder, with the preform itself being compressed. Then the preform holder/preform combination is washed with acetone three times for 30 minutes, after which the combination is dried under vacuum, at a good 150° C. for three hours. Then the preform holder/preform combination is mounted on the gas injector, in such a manner that gas from the injector can only flow through the preform holder. The reactor chamber in which the preform is disposed is evacuated by suction, and the reactor chamber is brought to the desired temperature of 850° C. via the surrounding oven at a constant heating rate of 2° C./min.

When the reactor chamber has reached the desired temperature (measured with thermocouples), the pressure in the chamber is adjusted to the desired value of 50 Torr. The separate calcium precursor Ca(tmhd)$_2$ and fluorine precursor P(OCH$_3$)$_3$, which are located outside the reactor chamber, are heated to 210° C. and 80° C., respectively, so that their vapor pressures are sufficiently high. The carrier gas is passed through the precursors. The vapor flow is controlled with a calibrated "vapor source controller". Then the gas/vapor mixture is passed to the injector at a flow rate of 500 ml/min. Under the influence of the high temperature the vaporous reactants are converted to a solid material, precipitated on the fibers of the preform. Standard analyses show the precipitate formed consists substantially of hydroxyapatite.

What is claimed is:

1. A method for manufacturing a fiber-reinforced bioactive ceramic implant, comprising the steps of
   a) preparing a base form of continuous fibers having spaces therebetween constituting an open volume, and then
   b) infiltrating the base form with calcium- and phosphate-containing gas precursors by applying a gradient over said base form so that said gas precursors pass through said base form,
   c) exciting the gas precursors to form a solid ceramic product on all of the fibers throughout the base form, wherein the ceramic homogeneously fills the open volume to thereby densify the base form, wherein the infiltrating and exciting steps are carried out over a period of time limited so as to retain a desired degree of porosity.

2. A method according to claim 1, wherein the gas precursor comprises calcium bis-1,1,5,5,5-hexafluoro-2,4,-pentanedionate·triglyme or tetraglyme.

3. A method according to claim 1, wherein the gas precursor comprises a phosphorus source chosen from the group consisting of an alkyl phosphite, an alkyl phosphate, a phosphorus-chlorine compound and P$_2$O$_5$.

4. A method according to claim 1, wherein the fibrous material comprises continuous fibers.

5. A method according to claim 1, wherein the infiltrating step is carried out in a CVI reactor, at a temperature between 300 and 1200° C.

6. A method according to claim 5, wherein the pressure in the CVI reactor is between 1 mbar and 5 bar (abs.).

7. A method according to claim 1, further comprising the step of, prior to densification with chemical vapor phase infiltration, initially densifying the base form using a sol/gel technique.

8. The method of claim 1, wherein the gradient is chosen from the group consisting of a temperature gradient, a pressure gradient, and a combination thereof.

* * * * *